United States Patent [19]

Valliéres

[11] Patent Number: 5,186,946
[45] Date of Patent: Feb. 16, 1993

[54] DISINFECTANT WITH WIDE SPECTRUM GERMICIDAL ACTIVITY

[76] Inventor: Lucien Valliéres, 3001 Sherbrooke W., Ste. G03, Montréal, Québec, Canada, H3Z 2X8

[21] Appl. No.: 841,812
[22] Filed: Feb. 26, 1992
[51] Int. Cl.$^5$ .................. A01N 37/00; A01N 39/00; A61L 9/00; A61L 11/00
[52] U.S. Cl. ................... 424/613; 424/76.21; 424/76.6; 514/574; 514/578
[58] Field of Search ................ 424/613, 76.21, 76.6; 514/574, 578

[56] References Cited

U.S. PATENT DOCUMENTS 4,404,191 9/1983 Sporkenback et al. ............. 424/613

FOREIGN PATENT DOCUMENTS 1290243 8/1991 Canada .

OTHER PUBLICATIONS

Rasmussen, Scientific American Magazine Oct. 1989 pp. 66-73, "The Cycling of Calcium as an Intracellular Messenger".

Primary Examiner—Allen J. Robinson
Attorney, Agent, or Firm—Pierre Lespérance; Francois Martineau

[57] ABSTRACT

A disinfectant effective against substantially all bacteria, fungi, bacterial and fungal spores, and viruses. The disinfectant composition consists of: from 60 to 90% by weight of potassium monoperoxysulfate; from 2 to 10% by weight of malic acid; from 2 to 6 % by weight of sulfamic acid; from 0.25 to 3% by weight of EDTA Na$_2$; from 1 to 15% by weight of alkylated ether of polyethylene glycol; wherein a total of 100% by weight of the composition is obtained.

12 Claims, No Drawings

DISINFECTANT WITH WIDE SPECTRUM GERMICIDAL ACTIVITY

FIELD OF THE INVENTION

This invention relates to germicides effective against bacteria fungi, viruses and particularly against spores.

BACKGROUND OF THE INVENTION

It has long been known that perishable foods can be preserved by drying, by salting and by acid-producing fermentations, and that chlorinated lime (calcium hypochlorite) can be used to deodorize sewage and garbage (and wounds). Sterilization denotes the use of either physical or chemical agents to eliminate all viable microbes from a material, while disinfection generally refers to the use of germicidal chemical agents to destroy the potential infectivity of a material. Sanitizing refers to procedures used to simply lower the bacterial content of utensils used for food. Antisepsis refers to the topical application of chemicals to a body surface to kill or inhibit pathogenic microbes. Disinfectants are widely used for skin antisepsis in preparation for surgery.

Sterilization of microbes exhibits the kinetics of a first-order reaction, in which the logarithm of the number of survivors decreases as a linear function of time of exposure.

Bacteria are the smallest organisms that contain all the machinery required for growth and self-replication. A bacterium includes a rigid cell wall surrounding the cytoplasmic membrane, which itself encloses a single naked chromosome without a nuclear membrane. The cytoplasmic membrane consists primarily of a bi-layer of lipid molecules.

The fundamental criterion of bactericidal action is loss of the ability of the organism to propagate indefinitely, when placed in a suitable environment. Bactericidal action suggests microbe damage of various types, including the triggering of irreversible damage to the cytoplasmic cell membrane or irreversible impairment of the DNA (or viral RNA replication. Accordingly, sterilization is not identical with destruction of microbes. Additionally, it is understood that damage to nucleic acids (DNA or RNA) is not always irreversible, as it is known that ultraviolet light-induced damage to viral nucleic acids can be repaired by enzymatic and genetic mechanisms.

Strongly acid and alkaline solutions are actively bactericidal. Indeed, the pH range tolerated by most microorganisms extends over 3 to 4 units, generally between pH values of about 4.5 to 8; however, mycobacteria are relatively resistant.

At sufficiently high concentrations, many chemicals are bacteriostatic and even bactericidal. The term disinfectant is restricted to chemical agents that are rapidly bactericidal at low concentrations. In contrast to lethal radiations—which damage the DNA (or viral RNA)—and to most bactericidal chemotherapeutic agents—which interact irreversibly with various active metabolic systems—most disinfectants act either by dissolving lipids from the cytoplasmic membrane (detergents, lipid solvents) or by damaging proteins (denaturants, oxidants, alkylating agents, and sulfhydryl reagents). The rate of killing by disinfectants increases with concentration and with temperature. Different kinds of disinfectants must be used for different purposes, due to the very large variety of microbes.

Chlorine has been used as an antiseptic for more than a century. Chlorine combines with water to form hypochlorous acid, a strong oxidizing agent. Hypochlorite solutions are used to sanitize clean surfaces in the food and the dairy industries and in restaurants; and $Cl_2$ gas is used to disinfect water supplies and swimming pools.

Alkylating agents, e.g. ethylene oxide, replace the labile H atoms on $-NH_2$ and $-OH$ groups, which are abundant in proteins and nucleic acids (DNA, RNA), and also on $-COOH$ and $-SH$ groups of proteins. Indeed, ethylene oxide has proved to be the most reliable substance available for gaseous disinfection of dry surfaces. However, its use is more expensive and presents some hazard of residual toxicity (being mutagenic to bacteria and insects). Ethylene oxide is widely used to sterilize heat-sensitive objects: plasticware; surgical equipment; hospital bedding. These alkylating agents, in contrast to other disinfectants, are nearly as active against spores as against vegetative bacterial cells, because they can penetrate easily and do not require water for their action.

Cationic detergents, e.g. benzalkonium chloride, are known to be active against all kinds of bacteria. They act by disrupting the cytoplasmic membrane, causing release of metabolites (the cytoplasmic molecules of the cell); in addition, their detergent action provides the advantage of dissolving lipid films that may protect bacteria.

Fungi are similar to bacteria, yet one of their differences is that their nucleic acid, consisting of multiple chromosomes, is enveloped by a nuclear membrane. In some fungi (as in some bacteria), the cell wall is surrounded by an external capsular polysaccharide which, in the case of bacteria at least, protects the pathogenic microbe from phagocytosis and thus play a major role in determining virulence.

Spores are metabolic by-products in the life cycle of some bacteria and fungi, and are often very resistant to physical and chemical disinfectant agents. Spores contain one or several nuclei. Fungi produce a variety of exospores, including conidia, chlamydospores (thick-walled and very resistant), and sporangiospores. Bacteria produce endospores, i.e. sporeslocated within the cytoplasm of the parental cell.

Bacterial endospores are differentiated cells formed within a vegetative cell; they encase a genome in an insulating dehydrated vehicle that makes the cell ametabolic and resistant to various lethal agents, but permits subsequent germination in an appropriate medium. Spores are much more resistant than the parental (vegetative) cell to the lethal effect of heat, drying, freezing, toxic chemical s and electromagnetic radiations. Spores are formed by the invagination of a double layer of the cytoplasmic membrane, which closes off to surround a chromosome and a small amount of cytoplasm. A thin spore wall, and a thicker cortex with a much looser peptidoglycan, are synthesized between the two layers; outside the cortex is a protein coat, rich in disulfide cross-links and constituting up to 80% of the total protein of the spore. The keratin-like impervious properties of the coat account for the resistance to attack by deleterious chemicals, while the dehydration and the presence of a large amount of Calcium and dipicolinate contribute to the heat resistance.

A striking feature of spores is their huge content of $Ca^{++}$, for which active transport units appear in the membrane of the mother cell early during sporulation. Normally the $Ca^{++}$ is accompanied by a roughly equivalent amount of dipicolinic acid, which can chelate Ca++; dipicolinate is almost unique to bacterial spores and may constitute as much as 15% of their weight. Dehydration and ionic conditions are undoubtedly major factors in stabilizing spore proteins. Ca dipicolinate evidently plays a large role, by some as yet unknown mechanism, for its content markedly influences heat resistance. Recent research results point out to the control of calcium flow across the cytoplasmic membrane, thanks to a "calcium pump" assembly embedded into the bi-layer lipid membrane of cells and defining a calcium selective through-membrane channel ("The Cycling of Calcium as an Intracellular messenger", Scientific American, Oct. 1989).

A virus consists of a single nucleic acid (either DNA or RNA), and a protein shell or coat surrounding the nucleic acid; the complete viral particle is called a virion. Some viruses contain lipids and carbohydrates. Virions lack constituents fundamental for growth and multiplication, they never "grow": virions are by themselves metabolically inert. Virions multiply (replicate) only after cell-host invasion, and therefore are obligatory intracellular parasites. Hence, a virus is more than a simple nucleoprotein (a chemical substance), but not quite a microbe (a living entity); that is to say, a virus is not really "alive" as it is slightly short of the threshold of life as we define it.

Inactivation of virions is the permanent loss of infectivity. The exposure of a population of virions to a chemical (or physical) inactivating agent at a defined concentration for a limited time, results in the inactivation of a proportion of the virions; the others retain infectivity. Therefore, total inactivation cannot be reached with certainty. Viral-inactivating chemical agents include: lipid solvents (effective against enveloped but not naked virions), alkylating agents, e.g. ethylene oxide (effective against all virions); lipolytic enzymes (for some enveloped virions).

A variety of germicides are on the market because of patent rights. For example, Canadian patent 1,290,243 issued 8 Oct. 1991 to Thomas AUCHINCLOSS, is directed to a germicide composition comprising five ingredients: an inorganic halide (sodium chloride), an oxidising agent (potassium persulfate triple salt), sulfamic acid, an organic acid (malic acid), and an anhydrous alkali metal phosphate. Enhancement of the virucidal activity of the germicidal composition is claimed, due to alleged buffering and chelating effect of the alkali metal phosphate.

The AUCHINCLOSS patent relates to biocidal (bacteria, fungi, et al) and virucidal compositions. However, a number of drawbacks have been discovered by applicant with respect to such a germicide compound:

(a) it is not effective against bacterial and fungi spores;

(b) because it is based on the release of chlorine in contact with an oxidizing agent and with non reducible organic acids, it remains of limited scope of activity;

(c) because of the presence of chlorine ions in sewage, it may give rise to organochlorine derivatives (carcinogenic compounds) and therefore, is undesirable in sewage water;

(d) the release of phosphates by the biocidal compound will pollute sewage water, and again for this reason is undesirable in waste water;

(e) sodium alkyl sulfate linear, a high foaming agent, is also undesirable in sewage water, since it will substantially reduce the efficiency of the waste water treatment plants;

(f) the lowermost pH level obtained after use of the biocidal composition is not acid enough to meet actual standards of sewage water pH.

OBJECTS OF THE INVENTION

The gist of the invention is therefore to address the need for a wide-spectrum disinfectant composition which will be effective against bacteria, fungi, viruses, and particularly against bacterial and fungi spores.

A more specific object of the invention is to produce a disinfectant composition particularly effective against bacterial and fungi spores by disruption of the spore protein coat rich in disulfide cross-links.

DESCRIPTION OF THE INVENTION

Accordingly with the objects of the invention, there is disclosed a disinfectant composition consisting of; (a) from 60 to 90% by weight of potassium monoperoxysulfate; (b) from 2 to 10% by weight of malic acid; (c) from 2 to 6% by weight of sulfamic acid; (d) from 0.25 to 3% by weight of ethylene diamine tetraacetic acid disodium salt (EDTA $Na_2$); (e) from 1 to 15% by weight of alkylated ether of polyethylene glycol; wherein a total of 100% by weight of the composition is obtained. The disinfectant composition is sporicidal, bactericidal, fungicidal and virucidal, as Well as cleansing and deodorizing. That is to say, the present disinfectant composition will destroy the potential infectivity of bacteria, fungi, bacterial (endo)spores, and fungi (exo)spores, as well as inactivate substantially all viroids coming in contact therewith. The molality of the surfactant (alkylated ether of polyethylene glycol) should range between 25 and 80.

Preferably, potassium monoperoxysulfate range in weight between 77 to 88% of total composition, and most preferably, constitutes about 80%. Similarly, malic acid preferably ranges between 3 and 8%, and most preferably constitutes about 4% by weight of total composition. Similarly, sulfamic acid preferably ranges between 3 to 6%, and most preferably constitutes 4% by weight of total composition. Similarly, EDTA $Na_2$ preferably ranges between 1 and 2%, and most preferably constitutes 2% by weight of total composition. Similarly, alkylated ether of polyethylene glycol preferably ranges between 3 and 10%, and most preferably constitutes 10% by weight of total composition.

The present disinfectant composition has a wide spectrum of efficacy, while no phosphate is released The disinfecting system is based entirely upon decomposition of potassium monoperoxysulfate, by irreducible organic acids, thus releasing hydrogen peroxide and eventually oxygen. Again there is no contamination of sewage water by phosphate ions. The use of non-ionic detergent allows for penetration through the lipidic walls of some micro-organisms, thus reaching the nucleic avoid of the cell (or viroid) to damage same and therefore prevent growth (or viral replication). The further use of non-ionic detergent creates but a small amount of foam, avoiding the inhibition of performance of mechanical equipment used in the treatment of waste water and permits a high degree of degradation 90+%). No coloring or flavoring (polluting) agents are added.

Potassium peroxymonosulfate will oxidize halide ions into halogens, ferrous ions into ferric, manganous ions into manganic, and hydrogen peroxide into oxygen. Potassium peroxymonosulfate can initiate the free radical polymerization of typical vinyl monomers, e.g. vinyl acetate, ethyl acrylate, and acrylonitrile. Potassium peroxymonosulfate is currently used as a bleaching agent in denture cleansers, toilet-bowl cleaners, and laundry dry-bleachers. Potassium peroxymonosulfate is also known for use in removing chloramines in swimming pools and as a disinfectant.

Accordingly, the active ingredient in the present disinfectant composition is potassium peroxymonosulfate, in that a byproduct of the dilution reaction is the potassium hydrogen sulfate, which will lower the pH of the solution. Potassium sulfate is present within the triple salt, but is not directly involved in the above-noted reaction.

The use of organic acids gives rise to the formation of hydrogen peroxide, which disinfecting properties are well known. ($H_2O_2$ is also non pollutant) Malic acid is a fairly strong organic acid, and a good chelating agent of di- and trivalent metal ions. It is non toxic. Sulfamic acid is also a strong organic acid with low toxicity The EDTA $Na_2$ has been incorporated to the present disinfectant composition in order to chelate the magnesium and calcium ions, in view of:

(a) removing calcium ions, thus softening the water and enhancing the detersive (disinfecting) action;

(b) removing levulinic acid under the form of sodium levulinate, thus increasing likelihood of cytoplasmic membrane disruption and therefore easing access to the nucleic acid for the disinfecting action.

Moreover, the presence of an equal percentage of malic and sulfamic acid produces a close to ideal range of acidity, to ensure the complete release of hydrogen peroxide. Finally, the present disinfectant composition is freely soluble in cold, tepid or warm water, and it can be used at tremendous ranges of concentrations (from 1 to 20 g per 100 ml of solution).

Since the oxyethylenated glycol surfactant has a high power of wetting action and is non ionic, it will promote bacterial and fungus cytoplasmic wall disruption about the bi-layer lipid component thereof, thus releasing cytoplasmic metabolites and enabling inactivation of the growth-dependent nucleic acid.

The heart of the invention lies in the release of oxygen from synergistic effect of the various ingredients present in this disinfectant composition. Indeed, the organic acids ensure low pH levels, essential for continuous and lengthy release of oxygen from the oxidizing agent, potassium monoperoxysulfate. The chelating agent, EDTA $Na_2$ (ethylene diamine tetraacetic acid disodium salt) deprives microbes from levulinic acid and calcium ions, (thus inducing sporulation, when applicable). The low foaming surface active agent will facilitate penetration of the cytoplasmic membrane and will enable the active agent to reach the nucleic acid of the microbe.

Indeed, synergism is verified by the release of oxygen by the potassium peroxymonosulfate when in acidic medium, giving rise to formation of hydrogen peroxide and sulfuric acid. The malic and sulfamic acid provide at their selected concentrations proper acidic conditions.

The pH of a 1% weight by volume concentration of the composition is about 2.15. After contact with the waste, the pH goes up to about 6.5, depending on the nature of the material being treated, e.g. organic and body fluids, protein load. The end products are mainly potassium sulfate, resulting from the catalysis of potassium monoperoxysulfate, and sulfates of iron and sodium. Potassium, calcium and magnesium malate are also found, as is EDTA calcium There are no organochlorine products present because there are no halogenic ions in this composition. Any chlorine compound present in the waste material would be oxidized to hypochlorous acid and then to the halogen which would then combine with sulfamic acid to form chlorosulfonic acid and also combine with Na or K ions resulting in a chloride.

The disinfecting efficiency of the present composition has been verified by applicant during experiments conducted over a wide variety of microbes, to assess the disinfectant action of different formulations of the present composition:

(a) viruses: herpes, adenovirus, parvovirus, coronavirus, paramyxovirus, rhabdovirus, retrovirus.

(b) (bacterial) endospores: *clostridium sporogenes*.

(c) bacteria: *streptococcus faecal is, staphyl ococcus aureus, salmonella typhimurium, pseudomonas aeruginosa, salmonell a choleraesuis, escherichia coli, enterobacter spp., klebsiella pneumoniae, serratia marcescens*.

(d) fungi: *Candida albicans, aspergillus flavus, trichophyton mentagrophytes, penicillium spp.*

EXPERIMENT #1

Various microbes were submitted to a 5% weight by volume concentration of a germicide composition consisting of the following ingredients:
  potassium monoperoxysulfate: 80% by weight
  malic acid: 4% by weight
  sulfamic acid: 4% by weight
  EDTA $Na_2$ salt: 2% by weight
  alkylated ether of polyethylene glycol: 10% by weight The growth inhibition percentage rate of the microbes relative to defined contact time were as follows:
  *Serratia marcescens*: 99.999999% (10 minutes)
  *Escherichia coli*: 100% (30 min)
  *Klebsiella pneumoniae*: 100% (30 min)
  *Pseudomonas aeruginosa*: 100% (30 min)
  *Mycobacterium phlei*: 100% (30 min)
  Bacteriophage MS-2: 99.99944% (7 min)
  *Mycobacterium smegmatis*: 99 98154 (10 min)
  *Clostridium sporogenes* 99.9999984% (10 min)
  *Bacillus subtilis*: 99.9583333% (10 min)
  *Bacillus cereus*: 99.9858823% (10 min)
  *Bacillus stearothermophilus*: 99.2131147% (10 min)
  *Saccharomyces cerevisiae*: 99.999840% (10 min)

EXPERIMENT #2

Various microbes were submitted to a 5% weight by volume concentration of a germicide composition consisting of the following ingredients:
  potassium monoperoxysulfate: 80% by weight
  malic acid: 8% by weight
  sulfamic acid: 3% by weight
  EDTA $Na_2$ salt: 0.5% by weight
  alkylated ether of polyethylene glycol: 8.5% by weight The growth inhibition percentage rate of the microbes relative to defined contact time were as follows:
  *Serratia marcescens*: 100% (10 minutes)
  *Mycobacterium smegmatis*: 99.99769 (10 min)
  *Clostridium sporogenes*: 99.999972% (15 min)
  *Bacillus subtilis*: 99.9750% (10 min)
  *Bacillus cereus*: 99.99999% (10 min)
  *Bacillus stearothermophilus*: 98.4852459% (10 min)
  *Saccharomyces cerevisiae*: 99.992272% (10 min)

The present disinfectant (powder) composition is specifically for use in cleaning instruments, floors and bedding and generally speaking for use in hospitals, bio-medical research centers, health centers, veterinary hospitals and clinics. Contact with the skin is not recommended because of the high pH of the composition; however, it is not corrosive. It is freely soluble in cold water.

Directions for use can be summarized as follows:

(a) routine cleaning and disinfection: prepare and wash with a 0,5% by weight solution of the present composition (e.g , 25 g in 5 liters of water).

(b) terminal disinfection of various areas: wash carefully with a 1% solution of the present composition (e.g., 50 g in 5 liters of water).

(c) disinfection of laboratory ware: if heavily soiled, soak in a 1% solution for 10 minutes, then rinse with running water. If lightly soiled, use a 1% solution of the present composition.

(d) disinfection of ambient air: a mechanical or manual sprayer may be used (there is increased risk of infection caused by a high degree of humidity) to vaporize a 0.2% by weight solution of the present composition (e.g., 10 g in 5 liters of water). With spores or other highly resistant microbes, or where important organic loads (feces, blood, urine) are present, the concentration of the present disinfectant composition could be increased to 5% weight by volume, and the contact time, increased. Also, a 0.2% weight by volume solution of the present composition could be applied in the form of spray (manually or mechanically).

It is understood that a 1% solution of the present disinfecting solution is not irritating to the skin; however, contact with eyes and mucous membranes should be avoided. The present composition should be stored in a cool, dry place separate from other chemicals. A 1% solution of this disinfectant will lose 20% of its potency after ten days. It is best to use the solution within two days from dilution of the powder composition.

I claim:

1. A germicide composition for deodorizing, cleaning and disinfecting in a single application, consisting of:
   (a) from 60 to 90% by weight of potassium monoperoxysulfate;
   (b) from 2 to 10% by weight of malio acid;
   (c) from 2 to 6% by weight of sulfamic acid;
   (d) from 0.25 to 3% by weight of EDTA $Na_2$;
   (e) from 1 to 15% by weight of an alkylated ether of polyethylene glycol surfactant;
   a total of 100% by weight of the composition being obtained
   wherein said disinfectant is bactericidal, fungicidal, sporicidal and virucidal.

2. A disinfectant as defined in claim 1, wherein the molality of said alkylated ether of polyethylene glycol ranges between 25 and 80.

3. A disinfectant as defined in claim 2, wherein said potassium monoperoxysulfate ranges between 77 and 88% by weight of the total disinfectant composition.

4. A disinfectant as defined in claim 3, wherein said potassium monoperoxysulfate constitutes about 80% by weight of the total disinfectant composition.

5. A disinfectant as defined in claim 2, wherein said malic acid ranges between 3 and 8% by weight of the total disinfectant composition.

6. A disinfectant as defined in claim 5, wherein said malic acid constitutes about 4% by weight of the total disinfectant composition.

7. A disinfectant as defined in claim 2, wherein said sulfamic acid ranges between 3 and 6% by weight of the total disinfectant composition.

8. A disinfectant as defined in claim 7, wherein said sulfamic acid constitutes about 4% by weight of the total disinfectant composition.

9. A disinfectant as defined in claim 2, wherein said EDTA $Na_2$ ranges between 1 and 2% by weight of the total disinfectant composition.

10. A disinfectant as defined in claim 9, wherein said EDTA $Na_2$ constitutes about 2% by weight of the total disinfectant composition.

11. A disinfectant as defined in claim 2, wherein said alkylated ether of polyethylene glycol ranges between 3 and 10% by weight of the total disinfectant composition.

12. A disinfectant as defined in claim 11, wherein said alkylated ether of polyethylene glycol constitutes about 10% by weight of the total disinfectant composition.

* * * * *